(12) United States Patent
Wagner et al.

(10) Patent No.: US 12,678,230 B2
(45) Date of Patent: Jul. 14, 2026

(54) SYSTEM AND METHOD FOR PERCUTANEOUS NEEDLE INSERTION

(71) Applicant: Wisconsin Alumni Research Foundation, Madison, WI (US)

(72) Inventors: Martin Wagner, Madison, WI (US); Fred T. Lee, Jr., Madison, WI (US); James Louis Hinshaw, Middleton, WI (US); Giuseppe V. Toia, Verona, WI (US); Meridith A. Kisting, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 570 days.

(21) Appl. No.: 18/177,925

(22) Filed: Mar. 3, 2023

(65) Prior Publication Data

US 2024/0293181 A1 Sep. 5, 2024

(51) Int. Cl.
*A61B 34/10* (2016.01)
*A61B 17/34* (2006.01)

(52) U.S. Cl.
CPC .......... *A61B 34/10* (2016.02); *A61B 17/3403* (2013.01); *A61B 2034/107* (2016.02)

(58) Field of Classification Search
CPC ................. A61B 34/10; A61B 17/3403; A61B 2034/107
See application file for complete search history.

(56) References Cited

U.S. PATENT DOCUMENTS

| | | | |
|---|---|---|---|
| 10,482,606 B2 | 11/2019 | Higgins et al. | |
| 2012/0184844 A1* | 7/2012 | Gielen | A61B 5/062 600/424 |
| 2016/0070436 A1* | 3/2016 | Thomas | G06T 7/0012 715/771 |
| 2017/0000567 A1* | 1/2017 | Kim | A61B 10/0233 |
| 2017/0309069 A1 | 10/2017 | Thomas et al. | |
| 2022/0392065 A1* | 12/2022 | Min | A61B 8/5223 |
| 2023/0044620 A1 | 2/2023 | Shochat et al. | |

FOREIGN PATENT DOCUMENTS

ES          2755391          4/2020

OTHER PUBLICATIONS

Abolhassani, Niki, Rajni Patel, and Mehrdad Moallem. "Needle insertion into soft tissue: A survey." Medical engineering & physics 29.4 (2007): 413-431. (Year: 2007).*

* cited by examiner

*Primary Examiner* — Rachel L Roberts
(74) *Attorney, Agent, or Firm* — Boyle Fredrickson, S.C.

(57) ABSTRACT

A system and method for evaluating percutaneous needle pathways provides an automatic segmentation of local tissue structures and performs a weighting to rank a large number of paths to quickly identify clinically favorable choices.

19 Claims, 3 Drawing Sheets

SYSTEM AND METHOD FOR PERCUTANEOUS NEEDLE INSERTION

STATEMENT REGARDING FEDERALLY SPONSORED RESEARCH OR DEVELOPMENT

CROSS REFERENCE TO RELATED APPLICATION

Background of the Invention

The present invention relates to a system and apparatus for the insertion of needle-like instruments percutaneously into a patient, and in particular, to an apparatus allowing a comprehensive and rapid assessment of many different insertion trajectories.

Percutaneous insertion of needle-like probes into a patient is required in a variety of medical procedures including biopsies and ablations. Prior to such procedures, the physician determines an insertion trajectory, for example, by viewing medical images of the patient, for example, obtained using a computed tomography (CT) machine providing axial slice images. While viewing these images, the physician must consider a large number of factors determinative of a safe and effective procedure. These factors include the location of organs or other tissue structures that should be avoided, for example, large airways, vessels, bones, fissures, the heart, and the like. The physician also considers a set of other rules developed over years of experience and the experience of the physician's peers in performing specific procedures.

It is impractical for the physician to analyze all possible trajectories of a needle for a given procedure or to have experience with all procedures. As a practical matter, the difficulty of visualizing trajectories outside of the image plane of the medical images (typically axial) means that anatomically favorable paths are often not identified by the physician.

SUMMARY OF THE INVENTION

The present invention operates to automatically evaluate a comprehensive range of needle paths for a given identified target, in some cases being over 50,000 different paths. This global evaluation is made possible by identifying and applying a set of anatomical rules and physician rules to weight each trajectory and provide a ranking allowing the best paths to be quickly revealed. Preliminary investigations with respect to needle biopsies of lung tissue indicate a high degree of correlation of the ranking provided by the present invention to physicians (the correlation of median physician rating versus invention was 86% (p<0.0001)).

Specifically, the invention may provide a system for percutaneous needle insertion along a trajectory, the system including a user terminal including a graphic display and an electronic computer including a memory for holding volumetric medical image data including a needle target structure. The program may execute to display the volumetric medical image data to allow identification by a user of the terminal of the needle target structure and then to segment the volumetric medical data to identify subset volumes of critical body anatomy for avoidance during needle insertion. A set of trajectories are then evaluated over two dimensions of angular range through the target structure according to: (i) a set of anatomical rules assessing each needle trajectory with a likelihood of intersecting a critical body structure; and (ii) a set of physician practice rules assessing each needle trajectory with respect to angle and path length. The program outputs at least one needle trajectory according to an ordering of the needle trajectories as assessed by the anatomical rules and physician practice rules.

It is thus a feature of at least one embodiment of the invention to provide a comprehensive evaluation of needle trajectories possible by developing automatable anatomical and physician-based rules.

The output may provide a set of preferred multiple needle trajectories together with corresponding cost values, the cost values providing a quantitative representation of the evaluation of the set of trajectories according to the anatomical rules and physician practice rules.

It is thus a feature of at least one embodiment of the invention to assign quantitative values to the order of trajectories to assist the physician in comparing trajectories that may be ranked differently but close in quality.

In one embodiment, the program may further execute to receive a proposed trajectory by a physician and to match that trajectory to one of the needle trajectories and thereby output at least one alternative needle trajectory preferred over the proposed trajectory based on the ordering.

It is thus a feature of at least one embodiment of the invention to operate as a reference for the physician to confirm that his or her independently developed trajectory is optimal. In this respect the invention provides a backstop or second opinion and permits the invention to be used in novel situations where physician-developed trajectories may be superior.

In the above situation, the output to the physician may include a corresponding cost value for the proposed needle trajectory and at least one alternative needle trajectory.

It is thus a feature of at least one embodiment of the invention to allow the physician to determine whether alternative trajectories are meaningfully better.

The system may further include an electronically controlled needle guide, such as a robotic arm, a laser pointer, or needle tracking system, adapted to guide a needle according to at least one output needle trajectory.

It is thus a feature of at least one embodiment of the invention to promote real time trajectory planning and implementation, for example, using the planning images to at once develop the needle trajectories and to guide the needle insertion.

The medical imaging device may have a gantry positionable about a patient at a range of gantry angles defining slice planes, and the angular range of the considered trajectories may be limited to no more than the range of gantry angles.

It is thus a feature of at least one embodiment of the invention to ensure that the selected trajectory can be monitored during the insertion procedure.

The anatomical rules may include a weighting table associated with different anatomical structures and the weighting may control an ordering of the needle trajectories.

It is thus a feature of at least one embodiment of the invention to provide a transparent evaluation process having weights that reveal the underlying evaluation process.

The critical body structures may include the heart, trachea, esophagus, aorta, bone, intestine, nerves, mediastinum, and spine and spinal cord.

It is thus a feature of at least one embodiment of the invention to provide rules addressing important tissue structures broadly applicable to a large number of procedures, not just including pulmonary procedures.

The anatomical rules may penalize trajectories determined to intersect the critical body structures and/or identified to be proximate to but outside the critical body structures.

It is thus a feature of at least one embodiment of the invention to consider both damage to critical organs and tissue as well as risk of such damage when the trajectory is close to the organ or tissue.

The physician-rules may limit trajectory path length and trajectory angle with respect to tissue structures.

It is thus a feature of at least one embodiment of the invention to capture general physician experience, including as captured in medical literature, developed over years of physician practice.

One such rule may limit a deviation of the trajectory from a tissue surface such as the skin or the surface of an organ.

It is thus a feature of at least one embodiment of the invention to prevent skiving of the needle trajectory experienced by physicians.

In one embodiment, the segmentation provided by the invention may detect emphysematous blebs, for example, using a median filter and a threshold of Hounsfield units and size.

It is thus a feature of at least one embodiment of the invention to provide an automatable technique for detecting emphysematous blebs whose puncture may be dangerous for needle insertions through the lung.

These particular objects and advantages may apply to only some embodiments falling within the claims and thus do not define the scope of the invention.

DETAILED DESCRIPTION OF THE PREFERRED EMBODIMENT

Figure 1:
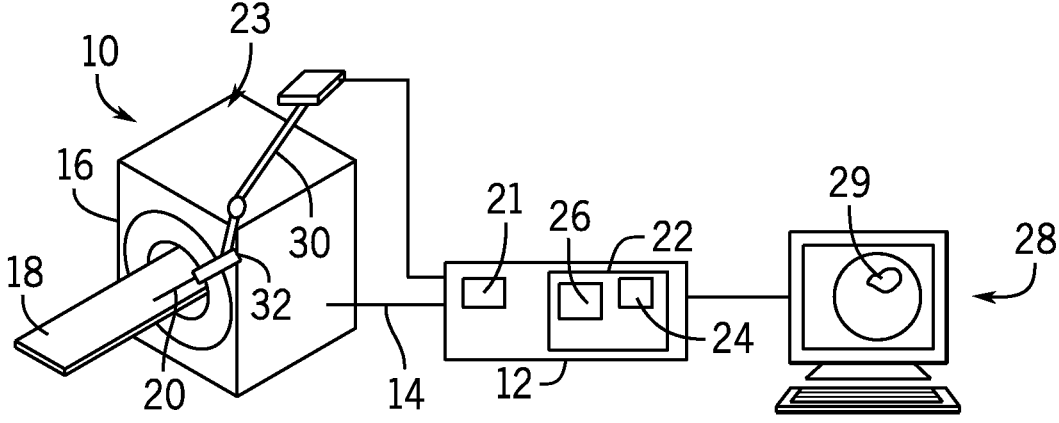
FIG. 1 is a block diagram of the principal components of the present invention including a volumetric medical image scanner, an electronic computer, a display terminal, and a robotic needle guide.
Figure 2:
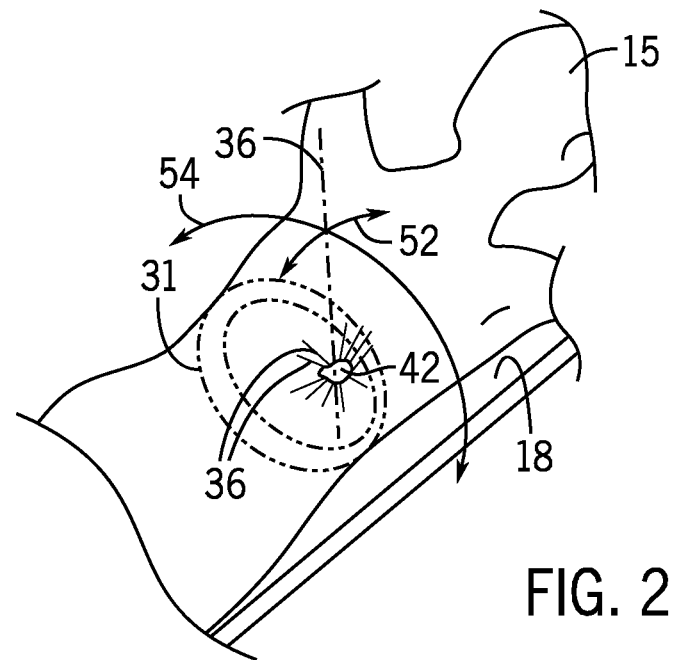
FIG. 2 is a perspective phantom view of a patient showing an axial slice volume holding target tissue and showing an angular range of possible needle trajectories that may be evaluated by the present invention.

Referring now to FIGS. 1 and 2, a system for percutaneous needle insertion 10, according to one embodiment of the invention may provide for an electronic processor 12 for receiving diagnostic image slice data 14 from an imaging machine 16. The imaging machine 16 may be, for example, a computed tomography (CT) machine operating to produce conventional computed tomography slice images and optionally to produce CT fluoroscopic images useful for near real-time visualization of a percutaneous needle 20 during insertion into the patient 15 (shown in FIG. 2). In some embodiments, the invention may use PET or functional MRI to produce comparable images.

The imaging machine 16 may include a patient support 18, for example, holding a patient 15 lying on the table surface and a gantry 23 including an x-ray source and opposed x-ray detectors for collecting projections that can be reconstructed into the slice data 14 for assembly into a volumetric image 31 of the patient 15.

The electronic processor 12 may include, for one or more processors 21 communicating with an electronic memory 22, holding a stored program 24 as will be discussed below. Electronic memory 22 may also hold volumetric image data 26 collecting the slice data 14 and describing a volume of patient tissue. The electronic processor 12 communicates with a user terminal 28 having a graphic display screen for the display of images 29 derived from the volumetric image data 26 and a keyboard or the like (not shown) receiving inputs from the physician with respect to the processing by the stored program 24.

Typically, the slice data 14 of each slice 31 will provide attenuation values (Hounsfield units) in a slice plane, for example, 1 to 1.5 mm thick, associated with a corresponding set of voxels demarcating regions of patient tissue. This slice plane is typically axial (perpendicular to the patient's superior-inferior axis) but can be tilted by a superior or inferior directed angle by tilting the gantry 23, for example, by plus or minus 20°. Multiple adjacent slice data 14 create the volumetric image data 26 which may allow reconstruction of images of slices at arbitrary angles through volume defined by the volumetric image data 26.

In some embodiments, the electronic processor 12 may further communicate with a needle guide 32 assisting in guiding the needle 20 along a selected trajectory 36. The needle guide 32 may be a robotic arm 30 or the like supporting a motorized needle insertion mechanism which mechanically guides the needle 20 along a predefined needle trajectory 36 under the control of program 24 and the physician. Alternatively, the needle guide 32 may present a guiding surface or a guiding laser beam following the desired needle trajectory or an electromagnetic tracking device monitored with respect to deviation from the desired trajectory by the program 24.

Figure 3:
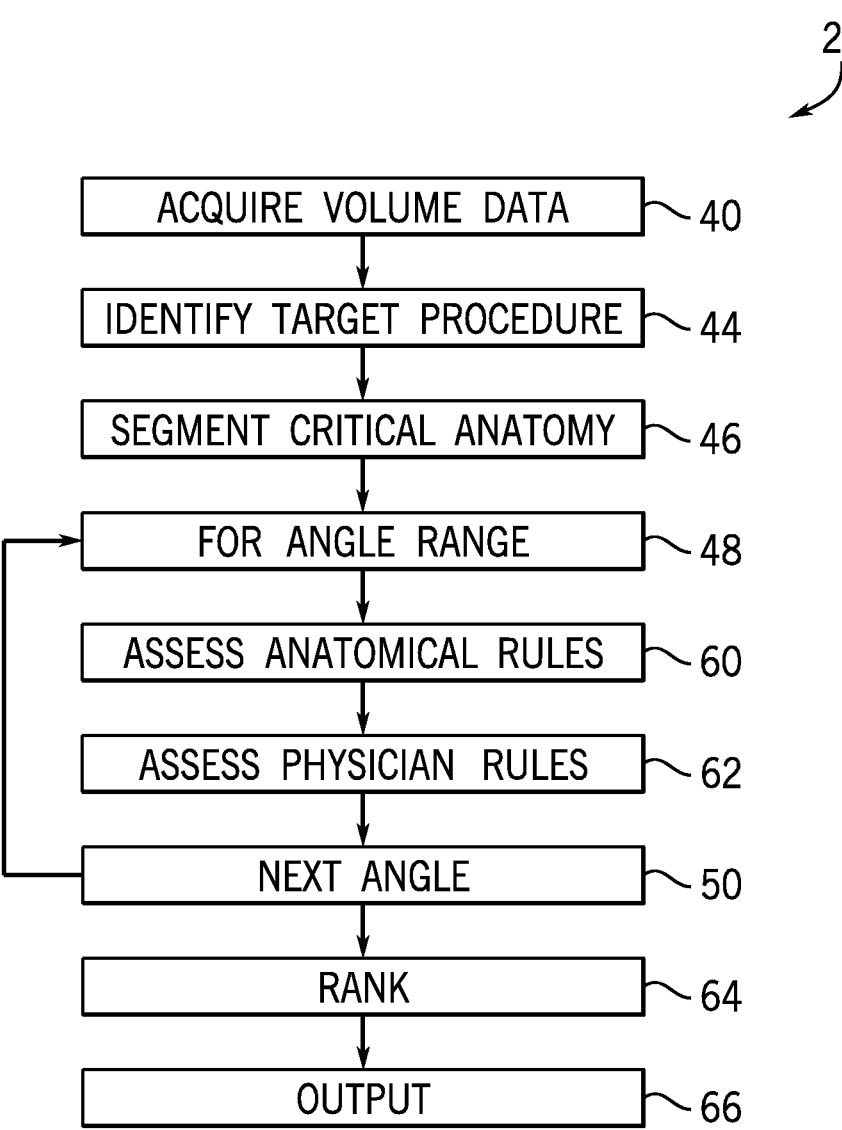
FIG. 3 is a flowchart of a program executed by the electronic computer of FIG. 1 for ranking needle trajectories.

Referring now also to FIG. 3, the program 24 operates, as indicated by process block 40, to first acquire volumetric image data 26 of a region of interest of the patient 15 including a target tissue 42, for example, a lesion, to be biopsied. The target tissue 42 and the particular procedure (e.g., biopsy, ablation) next may be identified by the physician viewing an image 19 derived from the volumetric image data 26 on the terminal 28 as indicated by process block 44. This identification may, for example, indicate center and radius of the target tissue 42.

At succeeding process block 46, the target tissue 42 and predefined critical tissue structures may be segmented, a process that determines the boundary of these structures and their locations. In one embodiment, the segmentation process may be performed by a machine learning system using a convolution U-net neural network, for example, as described in Ronneberger O, Fischer P, Brox T, U-Net: Convolutional Networks for Biomedical Image Segmentation in: Navab N, Hornegger J, Wells W M, Frangi A F, editors, Medical Image Computing and Computer-Assisted Intervention-MICCAI 2015 [Internet], Cham: Springer International Publishing; 2015 [cited 2022 Oct. 27], p. 234-41. (Lecture Notes in Computer Science; vol. 9351), available from: http://link.springer.com/10.1007/978-3-319-24574-4_28 and hereby incorporated by reference.

This segmentation will primarily identify organs and structures that can be readily visualized in the volumetric image data 26 but may also include structures that are not visible and yet critical, whose location is inferred from the segmentation of other anatomical landmarks. In this regard or alternatively, the segmentation may rely on functional imaging that defines structures and perform segmentations based on certain activity or functional response detected by a PET machine, functional MRI system, or the like, to produce a medical image.

Machine learning systems of this type may be trained using a set of manually segmented CT images of different organs, tissue types, and anatomic structures of interest including the heart, lung, pulmonary vessels and airways, muscle, bone, fat, fissures, and emphysematous blebs. Emphysematous blebs which represent abnormal air pockets of damaged lung tissue present a special case with respect to segmentation. In one embodiment the segmentation may identify tissue by applying a median filter to the volumetric image data 26, for example, with a 5×5×5 voxel kernel, and then thresholding voxels to select only voxels with a CT value of less than 950 Hounsfield units. After segmentation only structures having a volume equivalent to a sphere with a diameter of greater than 4 mm are identified.

As indicated by process blocks 48 and 50, the program 24 may then review a large set of possible needle trajectories 36 in a two-dimensional angular range along an inferior/superior direction 52 and circumferential direction 54 about the target tissue 42 for example describing trajectories 36 substantially evenly distributed to fill a solid angle. Typically the inferior/superior range will conform to the gantry angle range discussed above so that any selected trajectory 36 maybe imaged during the insertion process, for example, by x-ray fluoroscopy for conventional CT scanning. The circumferential direction 54 will typically be a range of 360° but may be usefully limited to 180° covering an arc overlying the patient 15 as positioned. The set of needle trajectories 36 may be evenly spaced, for example, at less than 1° (for example, 0.87°) and more than 10,000 or more than 50,000 trajectories 36 may be investigated in this loop.

As indicated by process block 60, each trajectory 36 may be first assessed against a set of anatomical rules. These rules consider the location of the critical body anatomy that should be avoided, assigning higher weights (costs) to trajectories 36 that intersect such critical body anatomy or are sufficiently close to such structures as to risk intersection. Example anatomical rules, for example, for a target tissue 42 such as a lesion in the lung, are indicated in Table I.

TABLE I

| Category | Structure or organ | Test | Weight |
|---|---|---|---|
| trajectory intersects structure or organ | heart/aorta | 1/0 (Yes/No) | infinite |
| | large vessels or airways (radius >= 1.5 mm) | 1/0 | 1 |
| | other organs | 1/0 | 3 |
| | fissures | 1/0 | 0.6 |
| | Emphysematous blebs | 1/0 | 0.8 |
| | ribs or bone | 1/0 | 3 |
| | spine | 1/0 | infinite |
| trajectory is close (distance) to intersecting structure or organ | heart/aorta | (10 mm − distance)/10 mm | 0.8 |
| | large vessels or airways (radius >= 1.5 mm) | (10 mm − distance)/10 mm | 0.8 |

The weights of the anatomical rules combine to produce a partial cost for each of the trajectories 36 being a sum of the test value times the weight for the relevant structures or organs. Thus, a trajectory that passed through bone and 5 mm from the heart would have a cost function of 3+(10− 5)/10*. 08 or 3.04.

As indicated by process block 62, the trajectory 36 is then evaluated against a set of physician-rules that, for example, consider trajectory angle and path length. Example physician-rules, for example, for a target tissue 42 in the lung, are indicated in Table II.

TABLE II

| Category | Trajectory or path length | Test | Weight |
|---|---|---|---|
| trajectory angle | angle (+90° to −90°) to axial plane | abs(angle/90) | 0.05 |
| | angle (+90° to −90°) to pleural surface | (90-angle)/90 | 0.25 |
| length of needle path | path through lung tissue | max (0, (length-10 mm)/10 mm) | 0.5 |
| | total path through tissue | max (0, (length-60 mm)/40 mm) | 1 |
| | path through minor vessels or airways(<1.5 mm) | 0.5 * length | 1 |

Generally, the rules related to trajectory angle represent physician experience that high angles may cause the needle to skive off of the trajectory in certain procedures. The total path length rules represent physician experience and intuition with respect to the degree by which longer path lengths for certain procedures can be associated with additional complications.

The weights of the physician rules again combine to produce a partial cost for each of the trajectories 36 being a sum of the test value times the weight for the trajectory or path length. Thus a trajectory that passed at 45° to the pleural surface, through 5 mm of lung tissue and 65 mm of tissue would have a cost function of (0.5*0.25)+(0)+(65/40) or 1.75. The partial costs for the anatomical rules and physician rules are added to produce a total cost, and at process block 64, the total cost is used to rank each of the analyzed trajectories 36.

Generally, different sets of physician rules and anatomical rules will be used with different procedures and selected at process block 44 described above.

Figure 5:
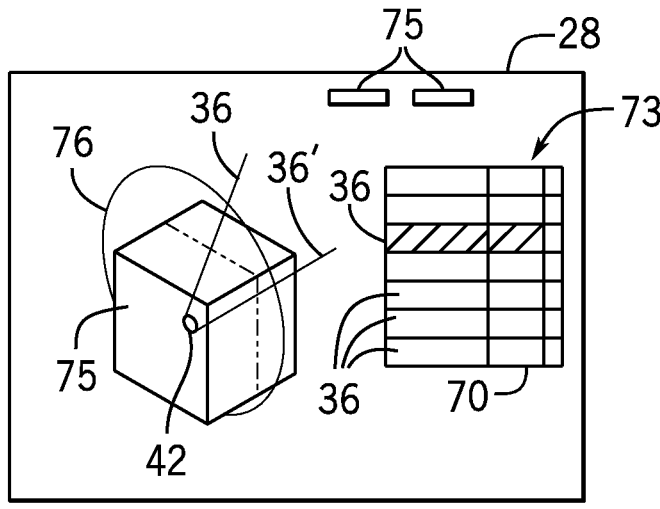
FIG. 5 is an example output display to the physician on the display terminal of FIG. 1.

Referring to FIGS. 3 and 5, at process block 66, the best trajectories 36 (lowest cost) may be presented to the physician on the terminal 28, for example, in a table 70 showing their ordering and the cost 73. Alternatively or in addition, the best trajectories may be displayed graphically in a rotatable model 75 of the volumetric image data 26 with respect to an axial plane 76 to clearly indicate the trajectory angles superimposed with the target tissue 42. A particular trajectory 36 may then be selected by the physician in the table 70 which will display or highlight the trajectory 36 on the rotatable model 75 or by selecting a representation of the trajectory 36 on the rotatable model 75. The selected trajectory 36 may be used to control the needle guide 32 and to adjust the tilt angle of the gantry 23 to bring the trajectory 36 into the plane of the image 29 and slice 31.

During the insertion procedure, the trajectory 36 may be displayed on a set up CT scan by registration of the trajectory 36 with that scan or by using this set up scan as the volumetric image data 26. The physician can select or reject any trajectories in the table 70 and then the next highest-rated trajectories may be displayed for consideration. Real-time imaging can also be used with CT imaging or fluoro imaging and the trajectory superimposed on these images during needle insertion. Needle angle and distance can be displayed in real time using the image data or data from the needle guide 32.

Figure 4:
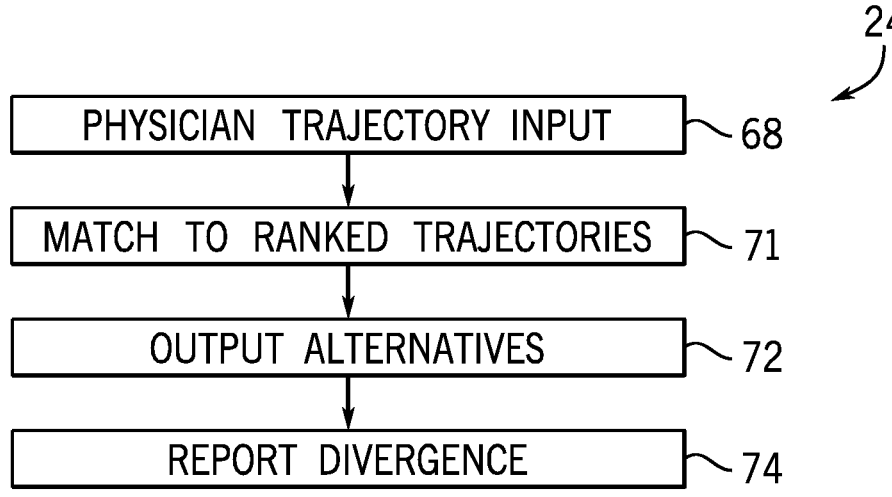
FIG. 4 is a flowchart of a program extension allowing physician input of a proposed trajectory for comparison to the ranked possible needle trajectories.

Referring now to FIGS. 4 and 5, in an additional embodiment, the physician may identify a preferred trajectory 36' as determined by the physician independently of the evaluation of the present invention as indicated by process blocks 68. This identification, for example, may be done by manipulating a graphical representation of the trajectory 36' on a representation of the volumetric image data 26, for example, using the rotatable model 75 showing the target tissue 42 and may display in real time quantitative data 75 indicating trajectory angle (inferior/superior and circumferential) and path length. The representation of the volumetric image data 26 may also provide for highlighted organ segmentation if desired.

At process block 71, this physician-developed trajectory 36' may be matched to a given one of the trajectories 36 evaluated in the loop of process blocks 48 and 50 shown in FIG. 3 and, based on the ranking of the matched trajectory 36, at process block 72, cause the outputting of the physician-preferred trajectory 36' together with its cost and one or more trajectories 36 identified in the process of FIG. 3 having improved costs. Again these trajectories 36 and 36' may be displayed graphically and/or in tabular form.

At process block 74, the physician may select one of these trajectories 36 or 36' to control the needle guide 32 and to adjust the gantry tilt to bring the trajectory 36 or 36' into the slice plane of the imaging machine 16. To the extent that there was a divergence between the recommended trajectories 36 derived per the program of FIG. 3 and the trajectory 36' ultimately selected by the physician or where the physician 36 selects one of the recommended trajectories 36 that is not a trajectory having the lowest cost, this difference may be logged and used to further develop the physician-based rules of Table II, for example, adjusting the weights.

Additionally, the volumetric image data 26, target tissue 42, and the trajectory 36 or 36', as accepted by the physician, may be recorded for use as a training set for a machine learning system directly to select trajectories 36 from volumetric image data 26. For both of these purposes, the physician may be prompted at process block 74 to indicate whether the procedure was successful (needle reaching the target) or a failure (complications such as pulmonary hemorrhage or pneumothorax). In some embodiments these conditions may be detected automatically and, in both cases, may provide for training of the present system or a future machine learning system.

It will be generally understood that the weighting system of the present invention can also be applied to the physician-preferred trajectory 36' alone, without the evaluation of other trajectories 36, to present the physician with an evaluation of that trajectory (for example, a single cost value, or a warning based on a predetermined cost threshold), as an effective second opinion.

In all of the cases described above, the component costs and their corresponding rules may be revealed to the physician (separately from the aggregate cost of the trajectory) to make the determination process transparent to the physician and to provide an indication to the physician of the particular rules contributing to the costs associated with the trajectory 36.

Generally, the program 24 will use different sets of anatomical rules and physician-rules for different procedures identified both in terms of the type of procedure and the target tissue 42. For example, in a biopsy, an additional physician rule may relate to increasing the path length through the target tissue and in lung biopsies; additional physician-rules are contemplated including favoring fat over muscle and favoring trajectories over ribs rather than under ribs, and generally avoiding bone because of the challenge of drilling through the bone. Additional anatomical rules may avoid the mammary and axillary vessels.

Certain terminology is used herein for purposes of reference only, and thus is not intended to be limiting. For example, terms such as "upper", "lower", "above", and "below" refer to directions in the drawings to which reference is made. Terms such as "front", "back", "rear", "bottom" and "side", describe the orientation of portions of the component within a consistent but arbitrary frame of reference which is made clear by reference to the text and the associated drawings describing the component under discussion. Such terminology may include the words specifically mentioned above, derivatives thereof, and words of similar import. Similarly, the terms "first", "second" and other such numerical terms referring to structures do not imply a sequence or order unless clearly indicated by the context.

When introducing elements or features of the present disclosure and the exemplary embodiments, the articles "a", "an", "the" and "said" are intended to mean that there are one or more of such elements or features. The terms "comprising", "including" and "having" are intended to be inclusive and mean that there may be additional elements or features other than those specifically noted. It is further to be understood that the method steps, processes, and operations described herein are not to be construed as necessarily requiring their performance in the particular order discussed or illustrated, unless specifically identified as an order of performance. It is also to be understood that additional or alternative steps may be employed.

References to "a microprocessor" and "a processor" or "the microprocessor" and "the processor," can be understood to include one or more microprocessors that can communicate in a stand-alone and/or a distributed environment(s), and can thus be configured to communicate via wired or wireless communications with other processors, where such one or more processor can be configured to operate on one or more processor-controlled devices that can be similar or different devices. Furthermore, references to memory, unless otherwise specified, can include one or more processor-readable and accessible memory elements and/or components that can be internal to the processor-controlled device, external to the processor-controlled device, and can be accessed via a wired or wireless network.

It is specifically intended that the present invention not be limited to the embodiments and illustrations contained herein and the claims should be understood to include modified forms of those embodiments including portions of the embodiments and combinations of elements of different embodiments as come within the scope of the following claims. All of the publications described herein, including patents and non-patent publications, are hereby incorporated herein by reference in their entireties.

To aid the Patent Office and any readers of any patent issued on this application in interpreting the claims appended hereto, applicants wish to note that they do not intend any of the appended claims or claim elements to invoke 35 U.S.C. 112(f) unless the words "means for" or "step for" are explicitly used in the particular claim.

What we claim is:

1. A system for percutaneous needle insertion along a trajectory comprising:

a user terminal including a graphic display; and an electronic computer including a memory for holding volumetric medical image data including a needle target structure and a stored program executing to:

display the volumetric medical image data to allow identification by a user of the terminal of the needle target structure;

segment the volumetric medical data to identify subset volumes of predetermined body anatomy for avoidance during needle insertion;

evaluate a set of trajectories over two dimensions of angular range through the needle target structure according to:

(i) a set of anatomical rules assessing each needle trajectory with a likelihood of intersecting a predetermined body structure and trajectory length; and (ii) a set of physician practice rules different from the anatomical rules assessing each needle trajectory; and output at least one needle trajectory according to an ordering of the needle trajectories as assessed by the anatomical rules and physician practice rules; and wherein the physician rule assesses a trajectory length through a specified tissue occurring along only a portion of the trajectory length through tissue.

2. The system of claim 1 wherein the output provides a set of preferred multiple needle trajectories together with corresponding cost values, the cost values providing a quantitative representation of the assessment of the set of trajectories according to the anatomical rules and physician practice rules.

3. The system of claim 1 wherein the program further executes to receive a proposed trajectory by a physician and to match that trajectory to one of the needle trajectories and to output at least one alternative needle trajectory preferred over the proposed trajectory based on the ordering.

4. The system of claim 3 wherein the output includes corresponding cost values for the proposed needle trajectory and the at least one alternative needle trajectory.

5. The system of claim 1 further including an electronically controlled needle guide adapted to guide a needle according to the at least one output needle trajectory.

6. The system of claim 5 wherein the needle guide is selected from the group consisting of a robotic guide arm, robotic laser pointer, and a needle tracking system.

7. The system of claim 1 further including a medical imaging device having a gantry positionable about a patient at a range of gantry angles defining slice planes and wherein the angular range is limited to no more than the range of gantry angles.

8. The system of claim 1 wherein the anatomical rules include a weighting table associated with different anatomical structures and wherein weights of the weighting table control an ordering of the needle trajectories.

9. The system of claim 1 wherein the predetermined body structure include heart, aorta, bone, and spine.

10. The system of claim 1 wherein the anatomical rules penalize trajectories determined to intersect the predetermined body structures.

11. The system of claim 1 wherein anatomical rules also penalize trajectories identified to be proximate to but outside the predetermined body structures.

12. The system of claim 1 wherein the physician practice rules describe limiting trajectory path length and limiting trajectory angle with respect to tissue structures.

13. The system of claim 1 wherein the anatomical rules limit a deviation of the trajectory from a tissue surface.

14. The system of claim 1 wherein the target structure is a lung malignancy.

15. The system of claim 14 wherein the predetermined structure includes emphysematous blebs and airways greater than 1.5 mm in radius.

16. The system of claim 15 wherein a segmentation of emphysematous blebs employs a median filter, a threshold of Hounsfield units, and a size threshold.

17. The system of claim 1 wherein the physician rule assesses an angle of the trajectory with respect to an organ surface.

18. A system for percutaneous needle insertion along a trajectory comprising:

a user terminal including a graphic display; and an electronic computer including a memory for holding volumetric medical image data including a needle target structure and a stored program executing to:

display the volumetric medical image data to allow identification by a user of the terminal of the needle target structure;

segment the volumetric medical data to identify subset volumes of predetermined body anatomy for avoidance during needle insertion;

evaluate a set of trajectories over two dimensions of angular range through the needle target structure according to:

(i) a set of anatomical rules assessing each needle trajectory with a likelihood of intersecting a predetermined body structure and trajectory length; and (ii) a set of physician practice rules different from the anatomical rules assessing each needle trajectory; and output at least one needle trajectory according to an ordering of the needle trajectories as assessed by the anatomical rules and physician practice rules; and wherein the set of needle trajectories is greater than 10,000.

19. A system for percutaneous needle insertion along a trajectory comprising:

a user terminal including a graphic display; and an electronic computer including a memory for holding volumetric medical image data including a needle target structure and a stored program executing to:

display the volumetric medical image data to allow identification by a user of the terminal of the needle target structure;

segment the volumetric medical data to identify subset volumes of predetermined body anatomy for avoidance during needle insertion;

evaluate a set of trajectories over two dimensions of angular range through the needle target structure according to:

(i) a set of anatomical rules assessing each needle trajectory with a likelihood of intersecting a predetermined body structure and trajectory length; and (ii) a set of physician practice rules different from the anatomical rules assessing each needle trajectory; and output at least one needle trajectory according to an ordering of the needle trajectories as assessed by the anatomical rules and physician practice rules; and wherein the physician rule assesses relative proportions of fat and muscle along the trajectory.

\* \* \* \* \*